United States Patent [19]

Beschke et al.

[11] 4,169,951

[45] Oct. 2, 1979

[54] PROCESS FOR THE PRODUCTION OF SUBSTITUTED PYRIDINE (B)

[75] Inventors: Helmut Beschke; Heinz Friedrich, both of Hanau, Fed. Rep. of Germany

[73] Assignee: Deutsche Gold- und Silber-Scheideanstalt vormals Roessler, Frankfurt, Fed. Rep. of Germany

[21] Appl. No.: 830,982

[22] Filed: Sep. 6, 1977

[30] Foreign Application Priority Data

Mar. 23, 1977 [DE] Fed. Rep. of Germany ....... 2712694

[51] Int. Cl.² .................. C07D 213/02; C07D 213/08
[52] U.S. Cl. .................................. 546/250; 546/251; 546/252
[58] Field of Search .................... 260/290 P; 546/250, 546/251, 252

[56] References Cited

U.S. PATENT DOCUMENTS

| | | | |
|---|---|---|---|
| 2,877,228 | 3/1959 | Mahan | 260/290 P |
| 2,926,074 | 2/1960 | Berger | 260/290 P |
| 3,898,177 | 8/1975 | Beschke et al. | 260/290 R X |
| 3,917,542 | 11/1975 | Beschke et al. | 260/290 P X |
| 3,932,421 | 1/1976 | Minato et al. | 260/290 P |
| 3,960,766 | 6/1976 | Beschke et al. | 260/290 R X |

FOREIGN PATENT DOCUMENTS

655703   1/1963   Canada ................................. 260/290 P

OTHER PUBLICATIONS

Vereschagin et al., Russian Chemical Reviews, vol. 30, pp. 426 to 429 (1961).
Tschitschibabin, J. Prakt. Chem., vol. 107, pp. 122 to 126, (1924).
Parcell et al., J. Org. Chem., vol. 28, pp. 3468 to 3473 (1963).

*Primary Examiner*—John D. Randolph
*Attorney, Agent, or Firm*—Cushman, Darby & Cushman

[57] ABSTRACT

Pyridines substituted in the 2- and 3-positions by aromatic or heteroaromatic groups are prepared by reacting an aromatic or heteroaromatic substituted ketone which has at least one reactive methylene group adjacent to the keto group with an aliphatic oxo compound having a carbon to carbon ethylenic double bond on the carbon atom adjacent to the oxo group and ammonia in the presence of a dehydrating and dehydrogenating catalyst at a temperature of about 250° to 550° C.

18 Claims, 1 Drawing Figure

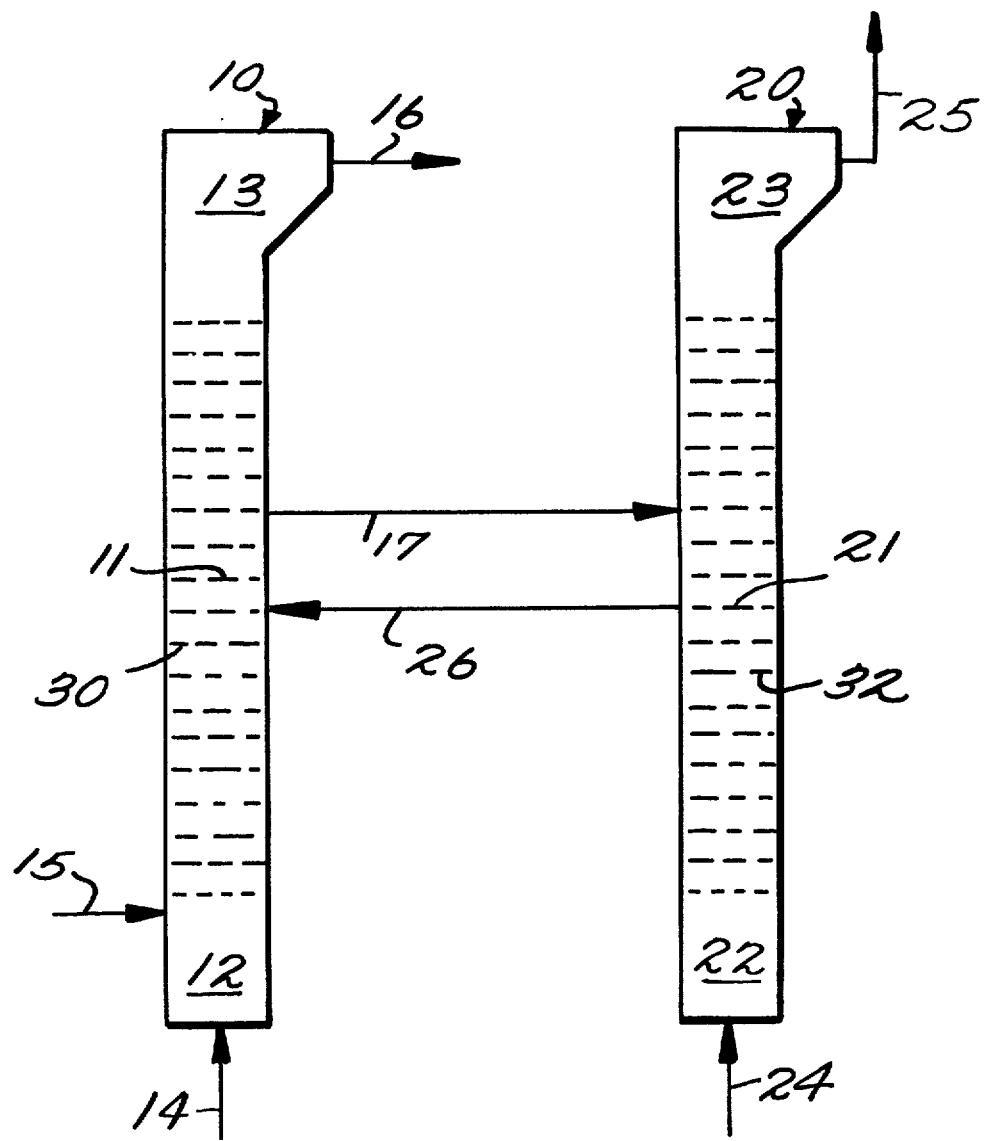

PROCESS FOR THE PRODUCTION OF SUBSTITUTED PYRIDINE (B)

BACKGROUND OF THE INVENTION

The invention is directed to a process for the production of pyridine substituted in the 2- and 3-positions by aromatic or heteroaromatic groups. These substituted pyridines are important intermediate products for the production of medicines, plant protective agents and synthetic resins.

It is known to produce pyridines having aromatic substituents in the 2- and 3-positions from ketones, namely, 2,3-diphenyl pyridine from desoxybenzoin and 2-benzyl-3-phenyl pyridine from 1,3-diphenylacetone. The ketone for this purpose is first converted to the enamine, this reacted with 3-bromo-propylamine hydrobromide in dimethyl formamide to the tetrahydropyridines and these finally dehydrogenated in the presence of palladium catalyst to the pyridines (Org. Chem. Vol. 28 (1963) pages 3468 to 3473). In the case of the production of 2,3-diphenyl pyridine from desoxybenzoin this can also be reacted with 3,3-diethoxy-1-dimethylamino-1-propene to form 5-dimethylamino-1,2-diphenyl-2,4-pentadien-1-one and this reacted with triethyloxonium tetrafluoroborate and further with dimethylamine to 5-dimethylamino-N,N-dimethyl-1,2-diphenyl-2,4-pentadieniminium-tetrafluoroborate and finally this converted into the 2,3-diphenyl pyridine by heating in an ammonium chloride-ammonia solution (Liebigs Ann. Chem. 1975 pages 874 to 900).

These processes are little suited for use in producing the substituted pyridines on an industrial scale. They are expensive and cumbersome to handle. Besides several of the necessary reagents are only available with difficulty.

SUMMARY OF THE INVENTION

There has now been found a process for the production of pyridines substituted in the 2- and 3-positions by aromatic or heteroaromatic groups by the catalytic reaction of an aromatic or heteroaromatic substituted ketone which has adjacent to the keto group at least one reactive methylene group with an aliphatic oxo compound which has an ethylenically unsaturated carbon to carbon double on the carbon atom adjacent to the oxo group in the gas phase and with ammonia and in the presence of a dehydrating and dehydrogenating catalyst at a temperature of about 250° to 550° C. In this process a pyridine substituted in the 2- and 3-positions by an aromatic or heteroaromatic group is produced in a one step reaction from readily available materials. High yields are produced. The process in contrast to the known processes is distinguished by being suited for use on an industrial scale.

According to the invention (1) an aromatic or heteroaromatic substituted ketone of the general formula $$R_2-CH_2-\underset{\underset{O}{\|}}{C}-(CH_2)_n-R_1 \quad (I)$$

in which $R_1$ and $R_2$ are the same or different and are an aromatic or heteroaromatic ring which in a given case is substituted by one or more halogen atoms, e.g., chlorine, bromine or fluorine, or alkyl, e.g., alkyl of 1 to 6 carbon atoms, or cyano and in which n is 0 or 1 with an oxo compound of the formula $$O=\underset{\underset{R_5}{|}}{C}-\underset{\underset{R_4}{|}}{C}=\underset{\underset{R_3}{|}}{CH} \quad (II)$$

in which $R_3$, $R_4$ and $R_5$ are the same or different and are hydrogen or lower alkyl group with preferably 1 to 6, especially 1 to 2, carbon atoms and in which in a given case the alkyl groups can be branched, and (3) with ammonia to form a compound of the general formula

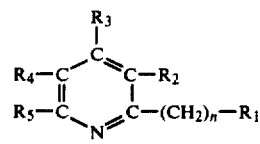

in which $R_1$, $R_2$, $R_3$, $R_4$ and $R_5$ are as defined above.

As aromatic or heteroaromatic substituted ketone (I) there can be used, for example, 4',4"-dichlorodiphenyl-1,3-acetone (also called 4,4'-dichlorodibenzyl ketone), dimethyldiphenyl-1,3-acetone, e.g., 4',4"-dimethyldiphenyl-1,3-acetone and 2',2"-dimethyldiphenyl-1,3-acetone, 2',2",4',4"-tetramethyldiphenyl-1,3-acetone, 4',4"-diethyldiphenyl-1,3-acetone, 4',4"-di-n-propyldiphenyl-1,3-acetone, 4',4"-di-n-butyldiphenyl-1,3-acetone, 4',4"-di-n-hexyldiphenyl-1,3-acetone, 4',4"-dibromodiphenyl-1,3-acetone, 2',2"-dichlorodiphenyl-1,3-acetone, 4',4"-difluorodiphenyl-1,3-acetone, 2',2",4',4"-tetrachlorodiphenyl-1,3-acetone, dicyanodiphenyl-1,3-acetone, e.g., 4',4"-dicyanodiphenyl-1,3-acetone, dipyridyl-1,3-acetone, e.g., 2',2"-dipyridyl-1,3-acetone, dithienyl-1,3-acetone, e.g., 2',2"-dithienyl-1,3-acetone, 4'-dipicolyl-ketone, 1',1"-dinaphthyl-1,3-acetone, 2',2"-difuryl-1,3-acetone, p-tolyl benzyl ketone, o-tolyl benzyl ketone, p-chlorophenyl benzyl ketone, p-bromophenyl benzyl ketone, p-cyanophenyl benzyl ketone, 4-chlorophenyl-4'-chlorobenzyl ketone, and particularly diphenyl-1,3-acetone, benzyl phenyl ketone, benzyl pyridyl ketone, e.g., benzyl 2-pyridyl ketone, picolyl phenyl ketone and benzyl thienyl ketone, e.g., benzyl 2-thienyl ketone.

Suitable oxo compounds are for example, methacrolein, methyl crotyl ketone, crotonaldehyde, methyl vinyl ketone, ethyl vinyl ketone, 3-penten-2-one, hexyl vinyl ketone, heptyl vinyl ketone, 3-octene-2-one, and especially acrolein.

The reaction conditions such as temperature and pressure and the proportions of the reacting substances and the residence time in a given case to a certain extent are dependent upon each other according to the type of reacting substances and the type of catalyst.

In general, the reaction is carried out at a temperature between 250° and 550° C. In most cases there are preferred temperatures between 300° and 500° C., especially between 350° and 450° C. It is advantageous to work at pressures of about 1 to 4 bar. However, there can also be used lower or higher pressures although it is suitable not to substantially deviate from this pressure range since it permits the use of simple apparatus.

The proportions of ketone (I) to oxo compound (II) can be selected substantially at random, both stoichiometric as well as under or over stoichiometric being usable. Generally, it is advantageous to add about 0.5 to 10 moles of oxo compound (II) per mole of ketone (I).

Preferably there are used about 1 to 5 moles, especially 2 to 4 moles of oxo compound (II) per mole of ketone (I).

The ammonia can be present in the reaction in substantially any proportions from under stoichiometric to over stoichiometric. In most cases it is suitable to have present at least 0.5 mole of ammonia per mole of ketone (I), however, there can be as much as about 100 moles of ammonia per mole of ketone (I). Advantageously, there are employed about 1 to 20 moles of ammonia, preferably 2 to 15 moles of ammonia, especially 3 to 12 moles of ammonia, per mole of ketone (I).

The reaction takes place in the gas phase. It can be expedient to dilute the gases of ketone (I), oxo compound (II) and ammonia with inert gases. As inert gases there can be employed, for example, steam, air and especially nitrogen. Generally, it is expedient to use in all not more than about 20 moles of inert gas per mole of ketone (I). Preferably, there are used about 0.5 to 10 moles, particularly 1 to 5 moles of inert gas per mole of ketone (I).

As catalysts there can be employed those which have a dehydrating and dehydrogenating action. For example, these include the catalysts described in Hydrocarbon Processing, Vol. 47 (1968) pages 103 to 107 which are aluminum compounds such as aluminum oxide and aluminum silicate, optionally with addition of other metal oxides and fluorides. The entire disclosure of the Hydrocarbon Processing article is hereby incorporated by reference and relied upon.

With advantage there is used in the process catalysts produced according to German Offenlegungsschrift No. 2 151 417 and related Beschke U.S. Pat. No. 3,898,177; according to German OS No. 2 224 160 and related Beschke U.S. Pat. No. 3,960,766; and according to German OS No. 2 239 801 and related Beschke U.S. Pat. No. 3,917,542. The entire disclosure of Beschke U.S. Pat. Nos. 3,898,177; 3,917,542 and 3,960,766 are hereby incorporated by reference and relied upon.

These catalysts are prepared by treating with oxygen at temperatures of 550° to 1200° C. compounds of the elements Al, F and O which compounds also contain at least one element of the second, third or fourth groups of the periodic system (German Offenlegungsschrift No. 2 151 417 and related Beschke U.S. Pat. No. 3,898,177) or at least two elements of the second, fourth, fifth or sixth groups of the periodic system (German Offenlegungsschrift No. 2 224 160 and related Beschke U.S. Pat. No. 3,960,766) or at least one element of the second main group of the periodic system (German Offenlegungsschrift No. 2 239 801 and related Beschke U.S. Pat. No. 3,971,542). The catalysts are used in a fixed bed or preferably in a fluidized bed.

Beschke U.S. Pat. No. 3,898,177 describes the catalyst in claim 1 as consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.:

1. aluminum, aluminum oxide or an aluminum compound convertible to the oxide at said temperature;

2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate;

3. Boron, silicon, boric oxide, silica or a compound of boron or silica convertible to the oxide at said temperature; and, 4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 1000:200, the atomic ratio of the total of boron and silicon to the other element from the second and fourth groups being between 1 to 10 and 10 to 1.

Beschke U.S. Pat. No. 3,917,542 in claim 1 describes the catalyst as having been prepared by heating at 600° to 800° C. In the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

Beschke U.S. Pat. No. 3,960,766 in claim 1 describes the catalyst as consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 2000.

Especially advantageous is a procedure using the apparatus and method of German OS No. 2 449 340 and related Beschke U.S. application Ser. No. 622,488 filed Oct. 15, 1975 in which instead of the reactants mentioned in the German OS and Beschke ketone (I) and oxo compound (II) are fed into the reactor separate from the ammonia. Generally, the residence time in the reactor is between 0.2 and 5.0 seconds. The entire disclosure of the Beschke U.S. application Ser. No. 622,488 is hereby incorporated by reference and relied upon.

The working up of the gas mixture resulting from the reaction can take place in customary manner by washing the gases with a liquid, especially water or methanol and by further separation by means of extraction and distillation. With especial advantage there is employed the procedure of German OS No. 2 554 946 and related Beschke U.S. application Ser. No. 748,041 filed Dec. 6, 1976 in which the gas mixture is not washed but cooled and as a result partially condensed in such manner that any possible excess ammonia remains in the residual gas and with this is directly recycled.

BRIEF DESCRIPTION OF THE DRAWINGS

The single FIGURE of the drawing is a schematic illustration of an apparatus suitable for carrying out the invention.

Referring more specifically to the drawing, there is used a tubular reactor 10 provided with cooling and heating devices (not shown). The reactor suitably contains in the middle portion 11 gas distribution plates 30, but in the lower part 12 and the upper part 13 there is free space. The first reaction gas is led into the reactor from below through line 14 and so regulated that the catalyst in the reactor forms a fluidized bed. The other reactant gases are led through line 15 into the fluidized bed. The reaction mixture is drawn off from the reactor in the upper part thereof through the line 16. A portion of the catalyst is always transported via line 17 from the reactor 10 to a regenerator 20. This regenerator also is advantageously constructed similar to the reactor 10. The regenerator also suitably contains gas distribution plates 32 in the middle portion but there is free space in the lower portion 22 and in the upper portion 23. The oxygen or oxygen containing gas is led into the regenerator 20 from below through line 24. The gas flow is so regulated that the catalyst present in the regenerator forms a fluidized bed. The gas escaping from the regenerator via line 25 is discarded. A portion of the catalyst is continuously relieved from the regenerator 20 via line 26 into the reactor 10.

Unless otherwise indicated all parts and percentages are by weight.

The process can comprise, consist essentially of or consist of the steps set forth and the materials can comprise, consist essentially of or consist of those set forth.

DESCRIPTION OF THE PREFERRED EMBODIMENTS

EXAMPLE 1

There was used the apparatus of the drawing (also disclosed in German OS No. 2 449 340 and Beschke U.S. application Ser. No. 622,488). Reactor 10 and regenerator 20 consisted of tubes 70 mm wide which had in their lower portions a free space 12 or 22 which was 200 mm high; thereover at intervals of 50 mm there were provided 40 wire screens with meshes of 5 mm (30 and 32) each in the spaces 11 and 21. There were provided above free spaces 13 and 23 having a height of 600 mm and a width of up to 160 mm.

There were led into the reactor 10 in gaseous form in uniform flow hourly from below via line 14 a gas mixture of 1500 normal liters (i.e., measured at standard pressure and temperature) of nitrogen and 1882 normal liters of ammonia. In a vaporizer there was prepared hourly a gas mixture from 1570 grams of acrolein and 325 normal liters of nitrogen. In a further vaporizer there was prepared a similar gaseous mixture from 2940 grams of dibenzyl ketone and 325 normal liters of nitrogen. These gaseous mixtures were combined and from the side via line 15 were led into the fluidized layer 130 mm above the bottom of the reactor at a temperature of 350° C.

The reactor contained 2.0 kg of catalyst which was produced according to Beschke U.S. Pat. No. 3,960,766 Example 1a (and German Offenlegungsschrift No. 2 224 160) from aluminum oxide, magnesium nitrate and titanium tetrafluoride and had an atomic ratio of aluminum to magnesium to titanium to fluorine of 1000:25:25:100. The catalyst had a particle size between 0.4 and 1.0 mm. The temperature in the reactor was held at 440° C. The reaction mixture leaving via line 16 was led at a temperature of 350° C. into a gas washing apparatus in which the 2-benzyl-3-phenyl pyridine and the pyridine and 3-methyl pyridine byproducts were washed out by means of methanol. The remaining residual gas of ammonia and nitrogen was recycled into the reactor.

The regenerator 20 contained an additional 2.0 kg of the catalyst. There were introduced into the regenerator from below via line 24 hourly 3000 normal liters of air. The temperature in the regenerator was held at 440° C. In a steady stream there were transferred hourly from the reactor to the regenerator 1.4 kg of catalyst and likewise there were returned 1.4 kg of catalyst from the regenerator to the reactor.

The dibenzyl ketone reaction was 100%. There were recovered hourly 2675 grams of 2-benzyl-3-phenylpyridine, 89 grams of pyridine and 365 grams of 3-methyl pyridine. This corresponds to a yield of 2-benzyl-3-phenylpyridine of 78%, based on the reacted dibenzyl ketone as well as 8% of pyridine and 28% of 3-methyl pyridine based on the acrolein added. The 2-benzyl-3-phenylpyridine had a boiling point of 146° to 150° C. at 1 mbar.

EXAMPLE 2

There was filled into a fixed bed reactor having a volume of 100 ml a catalyst which was produced according to Beschke U.S. Pat. No. 3,960,766 Example 1a (and German Offenlegungsschrift No. 2 224 160) from aluminum oxide, magnesium nitrate and titanium tetrafluoride and having an atomic ratio of aluminum to magnesium to titanium to fluorine of 1000:25:25:100. There were led over this catalyst hourly a gas mixture of 92 grams (0.44 mole) of dibenzyl ketone, 62 grams (1.1 moles) of acrolein, 69 normal liters (3.08 moles) of ammonia and 39 normal liters of nitrogen. The temperature in the reactor was held at 440° C. The dibenzyl ketone and the acrolein were completely reacted. There were recovered hourly 83 grams of 2-benzyl-3-phenyl-pyridine. This corresponds to a yield of 77% based on the dibenzyl ketone added. The product had a boiling point of 146° to 150° C. at 1 mbar. As byproducts there were formed 9% pyridine and 29% of 3-methyl pyridine based on the acrolein added.

In the following examples there was used the same procedure as in Example 2.

EXAMPLE 3

Starting Materials: benzyl phenyl ketone, acrolein and ammonia in the molar ratios of 1:2.3:6
Catalyst: As in Example 2
Reaction Temperature: 420° C.
Reaction: 100% of the benzyl phenyl ketone
Product: 2,3-diphenyl pyridine, B.P. 145° to 147° C. at 2 mbar
Yield: 62% based on the added benzyl phenyl ketone
Byproducts: 13% pyridine and 28% 3-methyl pyridine based on the acrolein added

EXAMPLE 4

Starting Materials: dibenzyl ketone, crotonaldehyde and ammonia in the molar ratios of 1:3:8
Catalyst: As in Example 2
Reaction Temperature: 400° C.
Reaction: 100% of the dibenzyl ketone
Product: 2-benzyl-3-phenyl-4-methyl pyridine, B.P. 155° to 157° C. at 2 mbar
Yield: 55% based on the added dibenzyl ketone

EXAMPLE 5

Starting Materials: benzyl phenyl ketone, crotonaldehyde and ammonia in the molar ratios of 1:2.7:7

Catalyst: As in Example 2
Reaction Temperature: 400° C.
Reaction: 100% of the benzyl phenyl ketone
Product: 2,3-diphenyl-4-methyl pyridine, B.P. 150° to 152° C. at 2 mbar
Yield: 46% based on the benzyl phenyl ketone added

EXAMPLE 6

Starting Materials: dibenzyl ketone, methyl vinyl ketone and ammonia in the molar ratios of 1:2:6
Catalyst: As in Example 2
Reaction Temperature: 410° C.
Reaction: 100% of the dibenzyl ketone
Product: 2-benzyl-3-phenyl-6-methyl pyridine, B.P. 154° to 156° C. at 2 mbar
Yield: 52% based on the dibenzyl ketone added

EXAMPLE 7

Starting Materials: benzyl phenyl ketone, methyl vinyl ketone and ammonia in the molar ratios of 1:2.3:6.5
Catalyst: As in Example 2
Reaction Temperature: 420° C.
Reaction: 100% of the benzyl phenyl ketone
Product: 2,3-diphenyl-6-methyl pyridine, B.P. 148° to 150° C. at 2 mbar
Yield: 48% based on the benzyl phenyl ketone added

EXAMPLE 8

Starting Materials: benzyl-2-pyridyl ketone, acrolein and ammonia in the molar ratios of 1:3:8
Catalyst: As in Example 2
Reaction Temperature: 410° C.
Reaction: 100% of the benzyl-2-pyridyl ketone
Product: 2-(2'-pyridyl)-3-phenylpyridine, B.P. 154° to 156° C. at 2 mbar
Yield: 34% based on the benzyl-2-pyridyl ketone added
Byproducts: 15% pyridine and 24% 3-methyl pyridine based on the acrolein added

EXAMPLE 9

Starting Materials: dibenzyl ketone, acrolein and ammonia in the molar ratios of 1.0:2.5:7.0
Catalyst: According to Beschke U.S. Pat. No. 3,898,177 Example 5 (and German OS No. 2 151 417) from aluminum oxide, magnesium nitrate and fluosilicic acid, atomic ratio aluminum to magnesium to silicon to fluorine of 1000:24:25:156
Reaction Temperature: 440° C.
Reaction: 100% of the dibenzyl ketone
Product: 2-benzyl-3-phenylpyridine, B.P. 146° to 150° C. at 1 mbar
Yield: 72% based on the dibenzyl ketone added
Byproducts: 12% pyridine and 31% 3-methyl pyridine based on the acrolein added

EXAMPLE 10

Starting Materials: dibenzyl ketone, acrolein and ammonia in the molar ratios of 1.0:2.5:7.0
Catalyst: According to Beschke U.S. Pat. No. 3,917,542 Example 1 (and German OS No. 2 239 801) from aluminum oxide, magnesium nitrate and ammonium hydrogen fluoride in the atomic ratio aluminum to magnesium to fluorine of 1000:25:50
Reaction Temperature: 440° C.
Reaction: 100% of the dibenzyl ketone
Product: 2-benzyl-3-phenylpyridine, B.P. 146° to 150° C. at 1 mbar
Yield: 74% based on the dibenzyl ketone added
Byproducts: 10% pyridine and 27% 3-methyl pyridine based on the acrolein added

What is claimed is:

1. A process for the production of a pyridine having a substituent from the group consisting of an aromatic group and a heteroaromatic group in each of the 2-and 3-position which comprises catalytically reacting a ketone having an aromatic or heteroaromatic group on both sides of the keto group and also having at least one reactive methylene group adjacent to the keto group with an aliphatic oxo compound having a carbon to carbon ethylenic double bond on the carbon atom adjacent to the oxo group and ammona in the gas phase at a temperature from about 250° to 500° C. in the presence of a dehydrating and dehydrogenating catalyst which is either (1) a catalyst consisting essentially of oxygen containing compounds of Al,F, at least one of the elements B and Si and at least one element from the second and fourth groups of the periodic system selected from the group consisting of Mg,Ba,Zn,Sn and Zr, said catalyst having been prepared by heating in the presence of oxygen at a temperature of 600° to 800° C.:
   1. aluminum, aluminum oxide or an aluminum compound convertible to the oxide at said temperature,
   2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
   3. boron, silicon, boric oxide, silica or a compound of boron or silicon convertible to the oxide at said temperature and
   4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 1000:200, the atomic ratio of the total of boron and silicon to the other element from the second and fourth group being between 1 to 10 and 10 to 1, (2) a catalyst having been prepared by heating at 600° to 800° C. in the presence of gaseous oxygen (1) aluminum metal, aluminum oxide or a compound of aluminum convertible to the oxide upon heating with gaseous oxygen at 600° C. to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system being selected from the group consisting of Mg, Ca, Sr and Ba, and (3) a catalyst consisting essentially of the product obtained by treating with oxygen at a temperature of 550° to 1200° C., compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1,000 to 10 and 1,000 to 800 and of Al to the elements of the second, fourth, fifth and sixth groups being between 1,000 to 5 and 1,000 to 200.

2. The process of claim 1 wherein the substituted pyridine has the formula

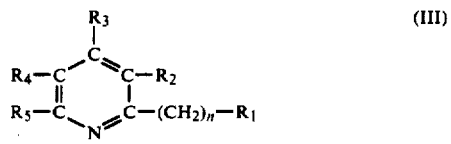

where $R_1$ and $R_2$ are aromatic or heteroaromatic rings which are unsubstituted or substituted by halogen, alkyl or cyanogen, $R_3$, $R_4$ and $R_5$ are hydrogen or lower alkyl and n is 0 or 1, the aromatic or heteroaromatic ketone has the formula

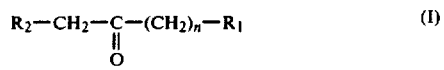

and the oxo compound has the formula

3. The process of claim 2 wherein $R_1$ and $R_2$ are unsubstituted phenyl, pyridyl or thienyl groups or such groups substituted by halogen, lower alkyl or cyano.

4. The process of claim 3 wherein $R_3$, $R_4$ and $R_5$ are hydrogen or alkyl with 1 to 2 carbon atoms.

5. The process of claim 4 wherein oxo compound (II) is acrolein.

6. The process of claim 2 wherein ketone (I) is dichlorodiphenyl-1,3-acetone, dimethyldiphenyl-1,3-acetone, dicyanodiphenyl-1,3-acetone, dipyridyl-1,3-acetone, dithienyl-1,3-acetone, diphenyl-1,3-acetone, benzyl phenyl ketone, benzyl pyridyl ketone, picolyl phenyl ketone or benzyl thienyl ketone and oxo compound (II) is methacrolein, crotonaldehyde, alkyl vinyl ketone having 1 to 2 carbon atoms in the alkyl group or 3-penten-2-one.

7. The process of claim 6 wherein ketone (I) is dibenzyl ketone, benzyl phenyl ketone or benzyl-2-pyridyl ketone and oxo compound (II) is acrolein, crotonaldehyde or methyl vinyl ketone.

8. The process of claim 7 wherein oxo compound (II) is acrolein.

9. The process of claim 7 wherein the process is carried out at 300° to 500° C.

10. The process of claim 2 wherein the reaction temperature is 300° to 500° C.

11. The process of claim 10 wherein the reaction temperature is 350° to 450° C.

12. The process of claim 2 wherein there is used 1 to 5 moles of oxo compound (II) per mole of ketone (I).

13. The process of claim 12 wherein there is used 1 to 20 moles of ammonia per mole of ketone (I).

14. The process of claim 13 wherein the reaction is carried out in the presence of an inert gas.

15. The process of claim 2 wherein the catalyst is aluminum silicate.

16. The process of claim 10 wherein the catalyst is (1).

17. The process of claim 10 wherein the catalyst is (2).

18. The process of claim 10 wherein the catalyst is (3).